United States Patent [19]
Talpade

[11] Patent Number: 6,086,527
[45] Date of Patent: *Jul. 11, 2000

[54] SYSTEM FOR TREATING CONGESTIVE HEART FAILURE

[75] Inventor: Dnyanesh Talpade, Plymouth, Minn.

[73] Assignee: Scimed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/054,214

[22] Filed: Apr. 2, 1998

[51] Int. Cl.$^7$ ..................................................... A61M 1/12
[52] U.S. Cl. .................................. 600/18; 600/16; 623/3
[58] Field of Search .......................... 600/16–18; 623/3; 604/101

[56] References Cited

U.S. PATENT DOCUMENTS

| | | |
|---|---|---|
| 3,455,298 | 7/1969 | Anstadt . |
| 3,791,374 | 2/1974 | Guarino ..................................... 600/17 |
| 4,407,271 | 10/1983 | Schiff ........................................ 600/17 |
| 4,536,893 | 8/1985 | Parravicini . |
| 4,685,446 | 8/1987 | Choy . |
| 4,781,716 | 11/1988 | Richelsoph . |
| 4,817,586 | 4/1989 | Wampler . |
| 4,834,707 | 5/1989 | Evans . |
| 4,846,831 | 7/1989 | Skillin . |
| 4,861,330 | 8/1989 | Voss . |
| 4,863,461 | 9/1989 | Jarvik . |
| 4,888,011 | 12/1989 | Kung et al. . |
| 4,902,291 | 2/1990 | Kolff . |
| 4,906,229 | 3/1990 | Wampler . |
| 4,919,647 | 4/1990 | Nash . |
| 4,925,377 | 5/1990 | Inacio et al. . |
| 4,925,443 | 5/1990 | Heilman et al. . |
| 4,938,766 | 7/1990 | Jarvik . |
| 4,957,477 | 9/1990 | Lundback . |
| 4,964,864 | 10/1990 | Summers et al. . |
| 5,067,960 | 11/1991 | Grandjean . |
| 5,069,680 | 12/1991 | Grandjean . |

(List continued on next page.)

FOREIGN PATENT DOCUMENTS

| | | |
|---|---|---|
| 0 654 283 A1 | 11/1994 | European Pat. Off. . |
| WO 98/17347 | 4/1998 | WIPO . |

OTHER PUBLICATIONS

"Mechanisms of Contraction", *Human Physiology,* Fourth Edition, by Stuart Ira Fox, pp. 300–323.

"The Management of Chronic Heart Failure", by Jay N. Cohn, M.D., *The New England Journal of Medicine,* pp. 490–498, Aug. 15, 1996.

"Reversal of Chronic Ventricular Dilation in Patients With End–Stage Cardiomyopathy by Prolonged Mechanical Unloading", by Howard R. Levin, M.D. et al., pp. 2717–2718, vol. 91, No. 11, Jun. 1, 1995.

"The Nature of the Atrial Receptors Responsible for a Reflex Decrease in Activity in Renal Nerves in the Dog", by R.J. Linden, D.A.S.G. Mary and D. Weatherill, *The Physiological Society,* 1980, pp. 31–40.

"Control of Sympathetic Nerve Activity by Vagal Mechanoreflexes is Blunted in Heart Failure", by Mark E. Dibner–Dunlap, M.D. and Marc D. Thames, MD, vol. 86, No. 6, Dec. 1992, pp. 1929–1934.

"Baroreflex Regulation of Regional Blood Flow in Congestive Heart Failure", by Mark A. Creager et al., *The American Physiology Society,* 1990, pp. H1409–H1414.

*Primary Examiner*—William E. Kamm
*Assistant Examiner*—George R. Evanisko
*Attorney, Agent, or Firm*—Westman, Champlin & Kelly, P.A.

[57] ABSTRACT

A system is provided for regulating blood flow to a portion of the vasculature, such as the renal system, in order to treat heart disease. A regulator maintains blood flow so as to control physiological feedback responses in order to relieve overload conditions on the heart.

17 Claims, 6 Drawing Sheets

U.S. PATENT DOCUMENTS

| | | |
|---|---|---|
| 5,089,019 | 2/1992 | Grandjean . |
| 5,098,442 | 3/1992 | Grandjean . |
| 5,119,804 | 6/1992 | Anstadt . |
| 5,131,905 | 7/1992 | Grooters . |
| 5,167,628 | 12/1992 | Boyles . |
| 5,205,810 | 4/1993 | Guiraudon et al. . |
| 5,290,227 | 3/1994 | Pasque . |
| 5,308,319 | 5/1994 | Ide et al. ................................... 600/18 |
| 5,308,320 | 5/1994 | Safar et al. . |
| 5,326,374 | 7/1994 | Ilbawi et al. . |
| 5,332,403 | 7/1994 | Kolff . |
| 5,358,519 | 10/1994 | Grandjean . |
| 5,364,337 | 11/1994 | Guiraudon et al. . |
| 5,383,840 | 1/1995 | Heilman et al. . |
| 5,429,584 | 7/1995 | Chiu . |
| 5,484,385 | 1/1996 | Rishton . |
| 5,505,701 | 4/1996 | Anaya Fernandez de Lomana . |
| 5,558,617 | 9/1996 | Heliman et al. . |
| 5,702,343 | 12/1997 | Alferness . |
| 5,755,779 | 5/1998 | Horiguchi . |
| 5,776,190 | 7/1998 | Jarvik ....................................... 600/16 |

SYSTEM FOR TREATING CONGESTIVE HEART FAILURE

BACKGROUND OF THE INVENTION

The present invention deals with treatment of heart disease. More particularly, the present invention deals with a system and method for treating heart disease by regulating blood flow in the vasculature.

Congestive heart failure is a common heart disease. The prevalence of incidents of congestive heart failure has recently increased, and there is considerable morbidity and mortality associated with its diagnosis. In fact, congestive heart failure is an extremely lethal disease with an estimated five year mortality for a vast majority of both men and women who encounter the disease.

Congestive heart failure results from loss of, or impairment of, normal heart function. This loss or impairment reduces cardiac output. This, in turn, results in a reduction in both blood flow and blood pressure in the kidneys. This reduction in flow and pressure causes a renin-angiotensin response that exacerbates congestive heart failure.

Briefly, as blood flow and pressure is reduced in the kidneys, cells in the kidneys referred to as juxtaglomerular apparatus secret an enzyme referred to as renin into the blood. The enzyme renin cleaves a ten-amino acid polypeptide called angiotensin I from a plasma protein in the blood called angiotensinogen. A converting enzyme in the blood removes two amino acids from the angiotensin I polypeptide leaving an eight amino acid polypeptide called angiotensin II. Angiotensin II has numerous effects on the smooth muscle layers of arterioles, including causing vasoconstriction. Further, an indirect effect of an increase in angiotensin II increases blood volume. Blood volume is increased because angiotensin II stimulates secretion of aldosterone from the adrenal cortex which, in turn, causes an increase in salt and water retention in the kidneys. Angiotensin II also stimulates thirst centers in the hypothalamus causing more water to be ingested. The increase in blood volume and the corresponding vasoconstriction cause an increase in blood pressure and hence a volume overload on the heart which causes further deterioration of the heart condition.

Another response is also related to congestive heart failure. Baroreceptors, referred to as stretch receptors, reside in the aortic arch and carotid sinuses. The baroreceptors are essentially pressure sensors sensing blood pressure in that area. The baroreceptors provide physiological feedback in two ways. First, in response to a reduction in blood pressure, the baroreceptors provide a neurohormonal feedback response which acts to increase the heart rate in an attempt to increase cardiac output. The increased heart rate causes the heart to work harder which, in turn, causes the heart muscle to stretch further. Also, a reduction in pressure caused by a reduction in cardiac output causes the baroreceptors to provide a feedback response which acts to constrict the distal vasculature thus increasing pressure in that area.

It can thus be seen that impairment of heart function can lead to a cyclical feedback response which increases, rather than reduces, the impairment. Such a cyclical feedback response is sometimes referred to as a cascade.

For instance, if the heart muscle is stressed, the heart works harder and begins to stretch. This reduces the efficiency of the heart. This inefficient or impaired heart function causes blood pressure in the areas of both the kidneys and the baroreceptors to decrease. The feedback response generated by the kidneys causes further overload and stress on the heart. The feedback response generated by the baroreceptors causes increased heart rate. Both of these feedback responses cause the heart to work harder, causing further stretching of the heart muscle and thus leading to greater inefficiencies. In response, the feedback responses become even more acute—and the cascade continues.

SUMMARY OF THE INVENTION

A system is provided for regulating blood flow to a portion of the vasculature, such as the renal system, in order to treat heart disease. A regulator maintains blood flow so as to control physiological feedback responses in order to relieve overload conditions on the heart.

In one embodiment, a system is provided for treating heart disease in a mammal having a heart, an ascending aorta, a descending aorta, and a renal system including renal arteries. The system includes a first regulator disposed in the ascending aorta and having an inflow end and an outflow end. The first regulator receives blood flow at a first velocity of the inflow end and provides blood flow at a second velocity through the outflow end thereof, wherein the second velocity is lower than the first velocity. A second regulator is disposed in the descending aorta upstream of the renal arteries. The second regulator has an inflow end and an outflow end and receives blood flow at a third velocity at the inflow end and provides blood flow at a fourth velocity through the outflow end thereof. The fourth velocity is greater than the third velocity.

In a second embodiment, a plurality of expandable members are placed across the renal arteries and/or baroreceptors to maintain blood flow and pressure to the renal arteries and/or baroreceptors and to thus inhibit undesirable responses from the renin-angiotensin system.

DETAILED DESCRIPTION OF THE PREFERRED EMBODIMENTS

Figure 1:
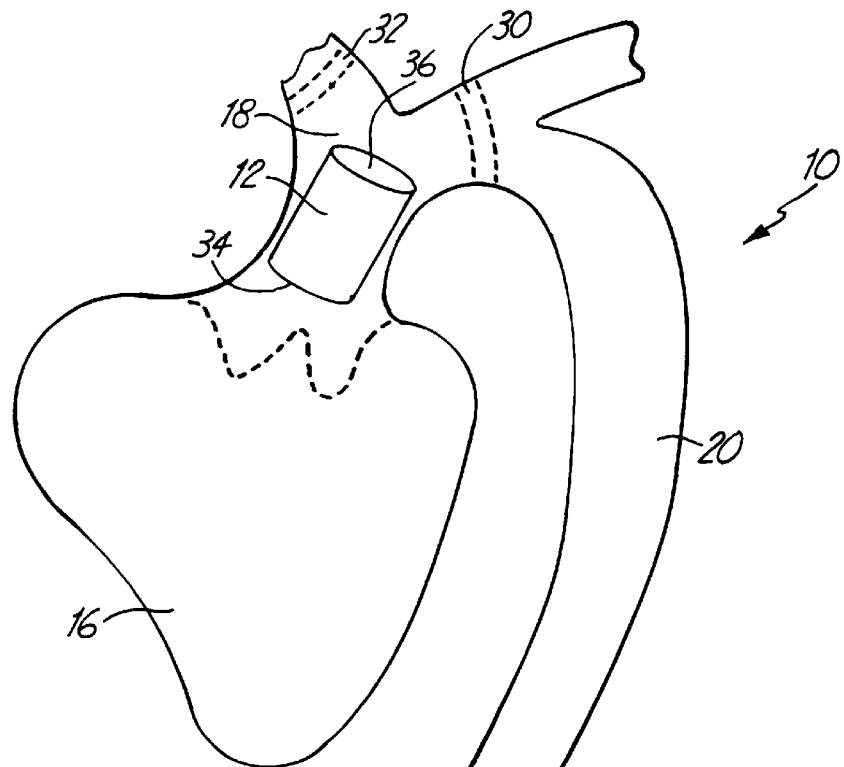
FIG. 1 illustrates a system for treating heart disease in accordance with one aspect of the present invention.
Figure 1:
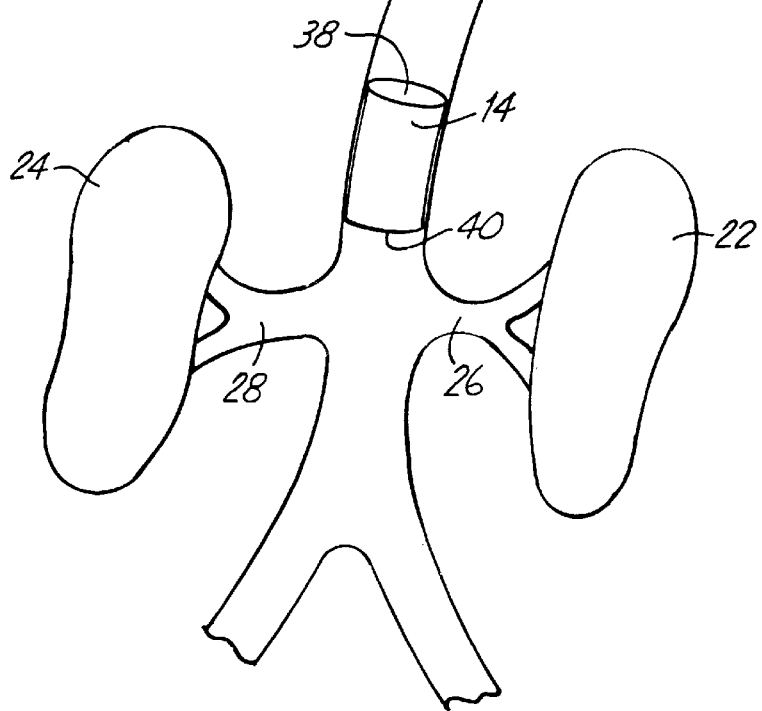

FIG. 1 illustrates a flow regulating system 10 in accordance with one aspect of the present invention. Flow regulating system 10 includes a first flow regulator 12 and a second flow regulator 14. Flow regulators 12 and 14 are placed in the vascular system of the patient, wherein the vascular system includes heart 16, ascending aorta 18, descending aorta 20, kidneys 22 and 24, and renal arteries 26 and 28. The vascular system also includes baroreceptors 30 and 32 located proximate ascending aorta 18.

Flow regulator 12 has an inflow end 34 and an outflow end 36. Blood from heart 16 flows into regulator 12 through inflow end 34 and flows out of regulator 12 through outflow end 36. The blood then travels through ascending aorta to the rest of the vasculature, including across baroreceptors 30 and 32, down descending aorta 20 and into flow regulator 14. The blood flows out of regulator 14 to the renal arteries 26 and 28.

In one preferred embodiment, flow regulator 12 regulates the velocity of blood flowing from heart 16 to the ascending aorta 18 by decreasing the velocity of the blood flow from a first velocity entering inflow end 34 to a lower velocity exiting outflow end 36. Regulator 14 also has an inflow end 38 and an outflow end 40. Regulator 14 regulates the velocity of blood flowing in the inflow end 38 and increases the velocity to a higher level as it flows through outflow end 40.

By reducing the velocity of blood flow from the inflow end 34 of regulator 12, through its outflow end 36, the velocity of blood flow encountered by baroreceptors 30 and 32 is lower as well. This induces a classic sympathetic nervous response. In other words, the blood pressure encountered by baroreceptors 30 and 32 will be reduced. This causes baroreceptor 30 and 32 to generate a neurohormonal response which calls for heart 16 to beat at an elevated rate and which induces vasoconstriction. This increases the mean arterial pressure in the vasculature.

However, since flow regulator 14 acts to increase the blood flow velocity therethrough, which acts to increase the blood pressure in renal arteries 26 and 28. This, in turn, inhibits the classic renal response to hypotension thus inhibiting the vascorestriction and increased blood volume associated with that response. This reduces the overload and stress on heart 16.

The overall reduction in stress on heart 16 allows passive rehabilitation of the myocardial system (i.e., the heart can repair itself). This also increases the efficiency of pharmacologically supplemented rehabilitation of the myocardium.

Flow regulators 12 and 14, in one preferred embodiment, are of similar construction. Flow regulator 12 acts as a step up regulator and flow regulator 14 acts as a step down regulator. However, as will be discussed later in the specification, regulators 12 and 14 can be substantially identical regulators, and can simply be positioned in the vascular system in 180° opposing relation to accomplish the desired step up or step down function.

Figure 2:
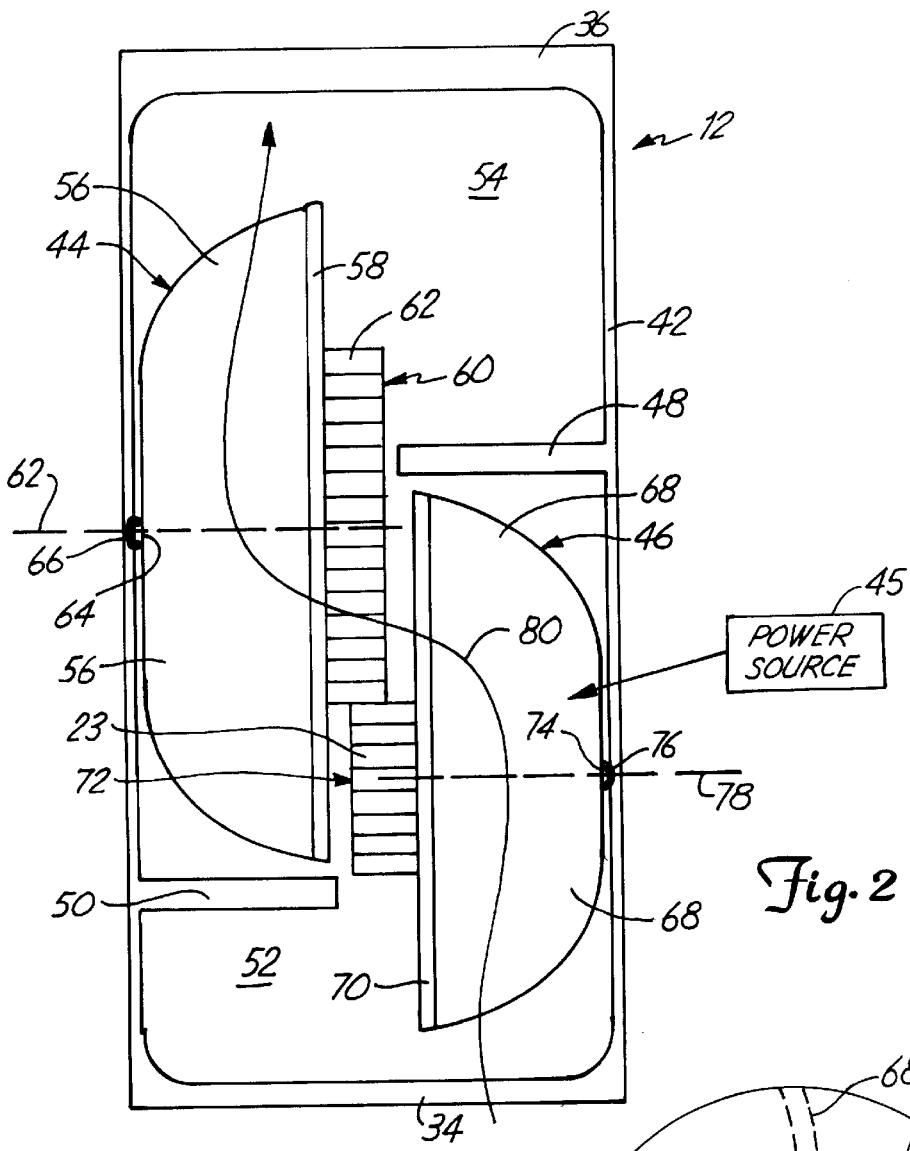
FIG. 2 is a top plan view of a pump in accordance with one aspect of the present invention.

FIG. 2 is a top plan view, taken in partial section, of flow regulator 12. It will be appreciated that flow regulator 14 is substantially identical to flow regulator 12, and therefore only flow regulator 12 will be described in detail. FIG. 2 illustrates that flow regulator 12 preferably includes a housing 42 which houses a pair of centrifugal pumping mechanisms 44 and 46. Also, housing 42 has a pair of walls 48 and 50 which, in combination with pumping members 44 and 46, act to separate housing 42 into two chambers including inflow chamber 52 and outflow chamber 54. Flow regulator 12 may also be provided with power source 45 (such as a motor) which can be coupled to one or both of pumping members 44 and 46 (such as through a drive shaft, belt, or other suitable connection mechanism) to provide active driving of the pumping members. Power source 45 is preferably a battery powered motor housed on or within housing 42 or is a remotely operable motor, operable by an actuator external to the body through wireless or wired connection. Such an actuator may, for example, be a power source for energizing motor 45 and selectively connectable to motor 45 through an operator operable switch with electrical connection being made to motor 45 with electrical conductors extending within the vasculature through a suitable catheter.

Pumping member 44 has a plurality of centrifugal fins 56 which are mounted to a first side of a generally circular base plate 58. A gear 60 having teeth 62 is mounted to a second side of base plate 58. Only two fins 56 are shown in FIG. 2. However, pumping member 44 preferably has three or more fins, as described later in the specification. Pumping member 44 is configured to rotate, orthogonal to the plane of the paper of FIG. 2, generally about an axis of rotation 62. Fins 56 are coupled to a thrust bearing 64 which is nested in a thrust bearing seat 66 on the wall of housing 42. Pumping member 44 spins about axis 62 with thrust bearing 64 bearing against thrust bearing seat 66.

Similarly, pumping member 46 is provided with a plurality of fins 68. As with pumping member 44, only two fins 68 are shown in FIG. 2, but pumping member 46 preferably has three or more fins. As with pumping member 44, fins 68 of pumping member 46 are disposed on a first side of a generally circular base plate 70, while a gear 72 having gear teeth 74 is disposed on the opposite side of base plate 70. Pumping member 46 also has a thrust bearing 74 which sits in a thrust bearing seat 76 in housing 42. Pumping member 46 is configured to rotate also orthogonally to the page of FIG. 2, about an axis of rotation 78 wherein thrust bearing 74 bears against thrust bearing seat 76 to accommodate such rotation.

The gear teeth 74 of gear 72 are engaged with the gear teeth 62 of gear 60 on pumping member 44. As illustrated in FIG. 2, gear 72 is smaller than gear 60. Thus, through the gear ratios applied by gears 72 and 60, pumping member 44 rotates at a slower speed than pumping member 46.

In operation, blood flow is generally indicated by arrow 80. Blood flows from heart 16 in through inflow end 34 into inflow chamber 52 of regulator 12. The blood encounters the fins 68 on pumping member 46 and causes pumping member 46 to rotate.

The blood flow, through rotation of fins 68 on pumping member 46, is brought into an internal chamber between walls 48 and 50. The blood flow then crosses over to pumping member 44. Rotation of pumping member 44 causes the blood to exit to outflow chamber 54, and eventually out through outflow end 36.

Since gear 72 is smaller than gear 60, pumping member 46 spins faster than pumping member 44. Therefore, blood enters through inflow chamber 52 at a first velocity and causes pumping member 46 to spin. However, the blood exits through outflow chamber 54 at a slower rate, because of the gear ratio applied by gears 60 and 72, which causes pumping member 44 to spin at a slower rate than pumping member 46. This operates to step down the velocity of the blood flowing through regulator 12. This results in reduced blood velocity reaching ascending aorta 18 and baroreceptors 30 and 32.

Figure 3:
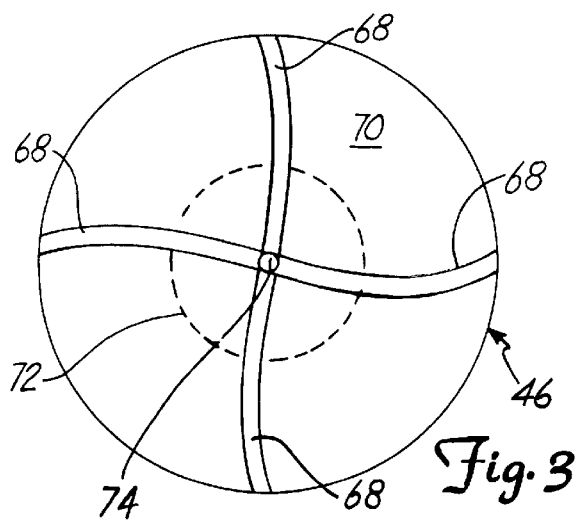
FIG. 3 is a side view of a portion of the pump shown in FIG. 2.

FIG. 3 is a side view of pumping member 46. It will be appreciated that pumping member 44 is similar to pumping member 46 (other than the difference in gear sizes) and therefore only pumping member 46 is described in detail. FIG. 3 illustrates that fins 68 are preferably curved to accomplish more efficient pumping of blood. FIG. 3 also illustrates that, in one preferred embodiment, fins 68 terminate in a center region of pumping member 46 at thrust bearing 74. Gear 72 is also shown in phantom in FIG. 3.

Figure 4:
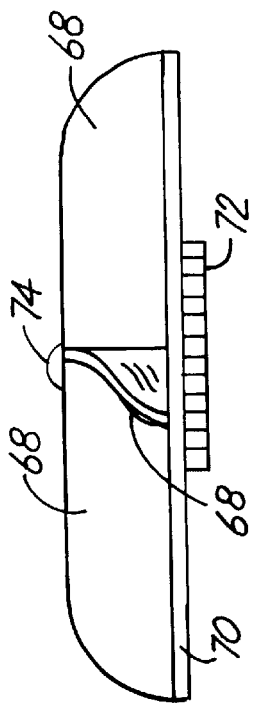
FIG. 4 is a side view of a portion of the pump shown in FIG. 3.

FIG. 4 is a side view of pumping member 46. FIG. 4 illustrates that the fins are preferably curved downwardly at a radial outward portion 82 thereof. This is to accommodate the curved shape of housing 42.

Figure 5:
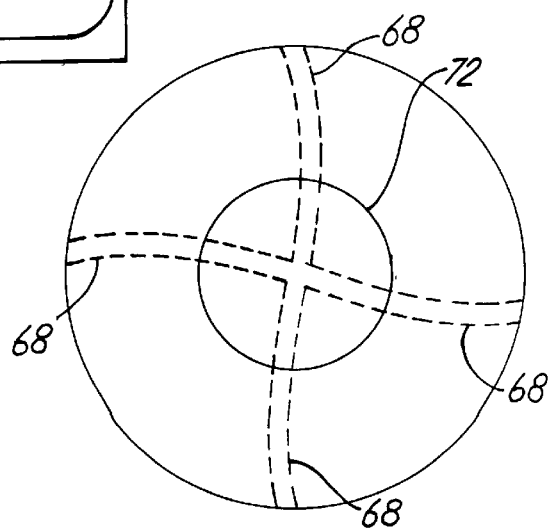
FIG. 5 is an opposite side view of a portion of the pump shown in FIG. 3.

FIG. 5 is another view of pumping member 46 showing the opposite side of that shown in FIG. 3. FIG. 5 also illustrates that gear 72 is preferably concentrically arranged about the axis of rotation 78.

Figure 6:
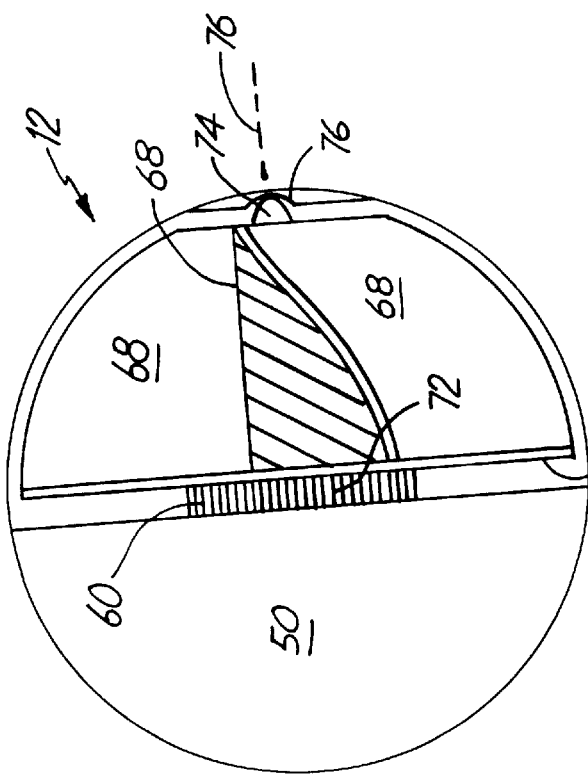
FIG. 6 is an end view looking into the pump illustrated in FIG. 2.

FIG. 6 is end view looking into flow regulator 12 from inflow end 34. FIG. 6 illustrates that wall member 50 is preferably hemispherical in shape and covers approximately half of the internal width of housing 42, in order to better define inflow chamber 52.

Flow regulator 14 is preferably substantially identical to flow regulator 12, except that it is rotated 180° within descending aorta 20. Thus, outflow end 36 of flow regulator 12 corresponds to inflow end 38 of flow regulator 14, and inflow end 34 of flow regulator 12 corresponds to outflow end 40 of flow regulator 14. Of course, blood flow through flow regulator 14 is in an opposite direction to that shown by arrow 80 in FIG. 2.

Flow regulator 14 acts to increase (or step up) blood flow velocity to renal arteries 26 and 28. This utilizes the physiological feedback response discussed above to reduce stress on the heart.

Active control of regulators 12 and 14 can be accomplished with the above-mentioned power source or motor 45. Such control can be obtained by synchronizing it to the sinus rhythms in much the same way as that described with respect to FIG. 8 below. Also, regulators 12 and 14 can be separately controlled to control blood flow and pressure to the baroreceptors and renal arteries separately. Also, the control pulses can be shaped so that flow and pressure are controlled smoothly rather than abruptly. Further, the geometry of the elements in regulators 12 and 14 can be changed to accomplish desired changes in flow characteristics therethrough. For instance, changing the diameter of the inflow and outflow ends changes the velocity of fluid flowing therethrough. Also, changing the shape of gears 60 and 72 (such as making them elliptical) changes the rotational characteristics of the pumping members 44 and 46. Further, either one or both of regulators 12 and 14 can be used.

Figure 7A:
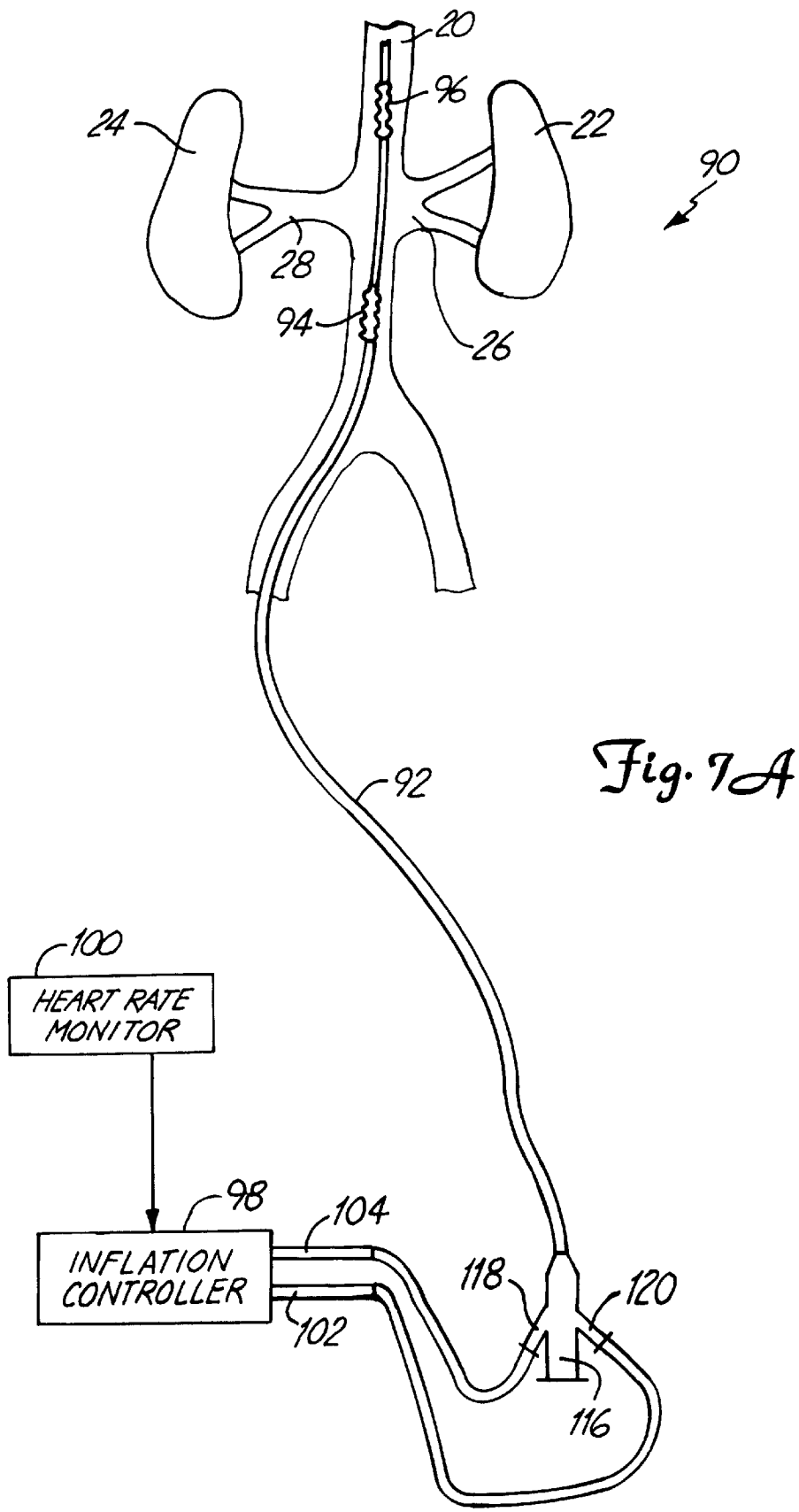
FIGS. 7A and 7B illustrate deployment of a blood flow regulating system in accordance with one aspect of the present invention.
Figure 7B:
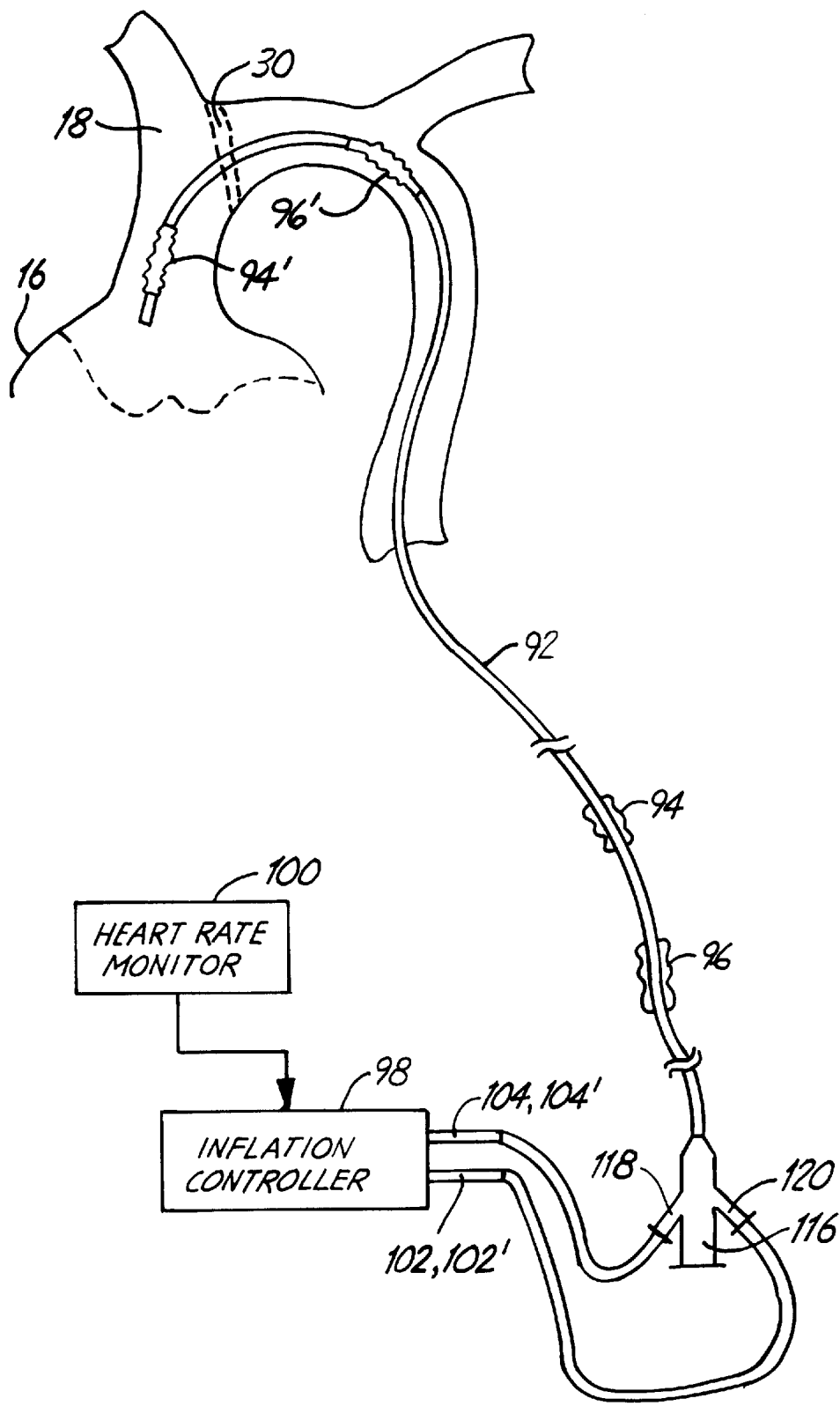

FIG. 7A illustrates a second embodiment of a system 90 for treating heart disease in accordance with another aspect of the present invention. System 90 includes balloons 94 and 96 (described below) and is shown disposed in descending aorta 20 proximate renal arteries 26 and 28. FIG. 7B shows that system 90 can include a second portion (with balloons 94' and 96') disposed proximate baroreceptors 30 and 32. The second portion operates similarly to the first portion described below, but the second portion acts to selectively increase or decrease flow to baroreceptors 30 and 32 as will be appreciated and will not be described in great detail for the sake of simplicity.

System 90 (as shown in FIG. 7A) includes a catheter 92 which has, at its proximal end, a first expansion member 94 and a second expansion member 96. System 90 also includes inflation controller 98 and heart rate monitor 100. Catheter 92 is preferably a multi-lumen catheter such that expandable members 94 and 96 (and 94' and 96') are expandable independently of one another. Thus, inflation controller 98 is preferably a pneumatic inflation device which has a pair of pneumatic outputs 102 and 104 (and two additional pneumatic outputs 102' and 104' for connection to balloons 94' and 96') which are connected to the lumens of catheter 92 which are, in turn, connected to inflation members 94 and 96 (as is described in greater detail with respect to FIG. 10). In operation, balloons 94 and 96 are inflated and deflated to increase blood flow to the renal arteries 26 and 28 in order to inhibit the renin-angiotensin response, and thus prevent fluid volume retention.

Figure 8:
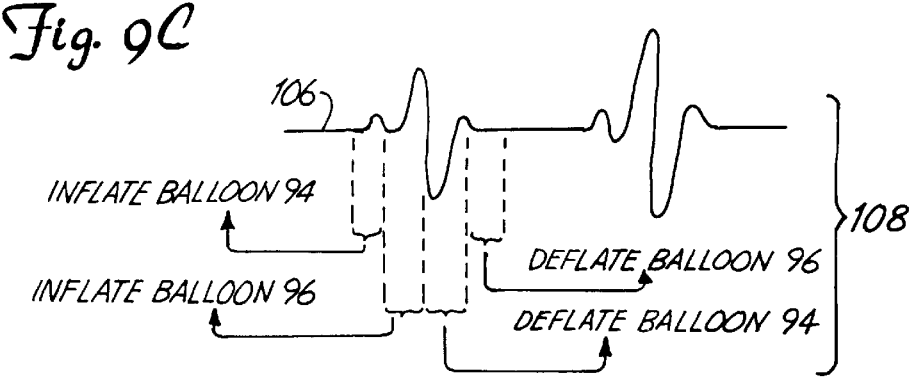
FIG. 8 is a plot of sinus rhythm against balloon inflations and deflations in accordance with one aspect of the present invention.

The operation of system 90 is described with respect to FIGS. 8 and 9A–9D. FIG. 8 illustrates a sinus rhythm 106 and a corresponding timing diagram 108. Only a portion of system 90 is shown in FIGS. 9A–9D for the sake of clarity.

Figure 9A:
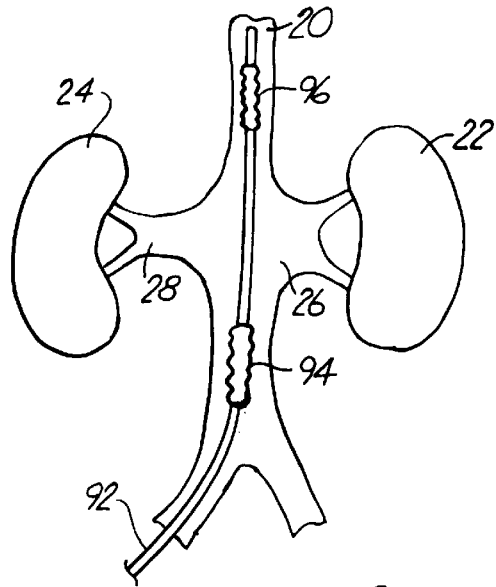
FIGS. 9A–9D illustrate operation of the system shown in FIG. 7.

Initially, catheter 92, with balloons 94 and 96, is introduced into the vascular system, such as through a femoral artery. Catheter 92 is positioned such that balloons 94 and 96 are placed across the renal arteries 26 and 28 as illustrated in FIG. 9A, with both balloons deflated. At systole, balloon 96 remains deflated while balloon 94 is inflated. This is shown in FIG. 9B, and causes a pool of blood 110 to be accumulated in the descending aorta in the region across renal arteries 26 and 28.

Figure 9B:
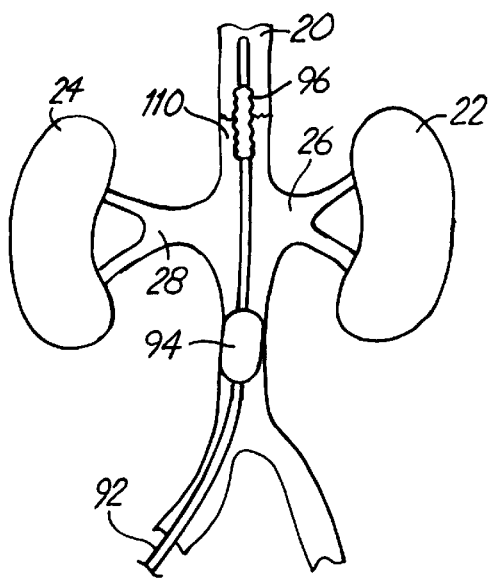
Figure 9C:
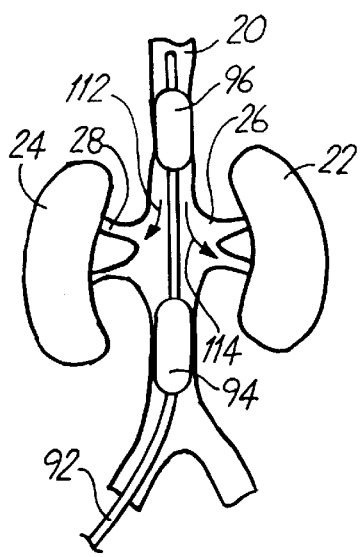

After a finite delay, balloon 96 is inflated as shown in FIG. 9C. As balloon 96 is inflated, the blood pressure between the balloons begins to increase, and blood is forced into renal arteries 26 and 28 as illustrated by arrows 112 and 114.

Figure 9D:
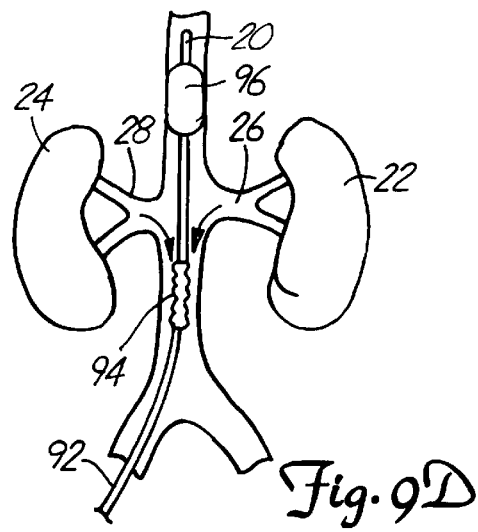

After balloon 96 has been inflated, or while balloon 96 is being inflated, balloon 94 is deflated as indicated in FIG. 9D. This functions to prevent excessive pressure and flow from being exerted on renal arteries 26 and 28. This allows the blood which had accumulated in the area of renal arteries 26 and 28 to escape from that region and continue flowing through the rest of the vasculature.

It should be noted that the entire inflation and deflation sequence shown in FIGS. 9A–9B takes place preferably in a time period less than one heart beat so that, at the next systole, the sequence can be repeated. The balloon inflation and deflation times, as well as the pressures and the inflation and deflation sequences, are gated to the patient's heartbeat through external heart rate monitoring equipment, such as heart rate monitor 100.

The increased blood flow to the renal system inhibits the renin-angiotensin system response and thus reduces the likelihood that any fluid volume retention will occur. Since little or no excess fluid volume is accumulated, there is a smaller load on heart 16. This allows heart 16 to passively recuperate, or it renders pharmacologically supplemented recuperation more efficient.

Figure 10:
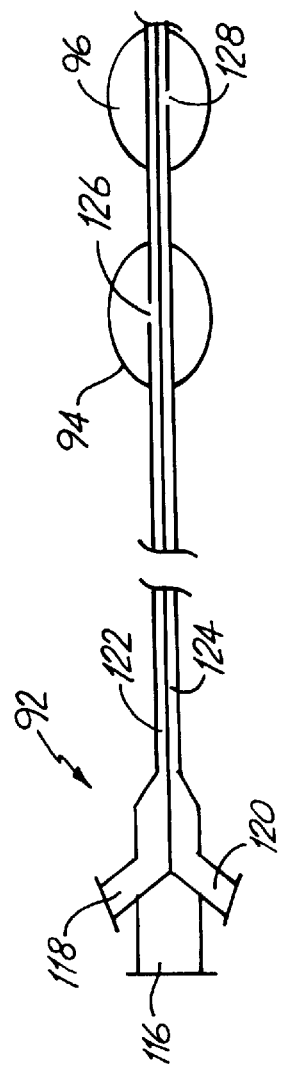
FIG. 10 illustrates a catheter implementing a portion of the blood flow regulating system shown in FIG. 7.

FIG. 10 is a more detailed view of catheter 92. In a preferred embodiment, catheter 92 includes a proximal hub 116 with a pair of proximal coupling members 118 and 120. Coupling members 118 and 120 are preferably coupled to a pair of lumens 122 and 124 within the body of catheter 92. Lumen 122 extends at least to balloon 94 and has an aperture 126 formed therein which fluidly communicates with balloon 94. Lumen 124 extends at least to balloon 96 and has an aperture 128 which fluidly communicates with the interior of balloon 96. Thus, as inflation controller 98 provides pneumatic pressure within lumens 122 and 124, balloons 94 and 96 can be inflated and deflated, as desired.

As described above, system 90 can be arranged proximate the renal system or the baroreceptors or both. Thus, blood flow in those areas can be controlled in a synchronous fashion, or entirely independently of one another.

Thus, it can be seen that the present invention provides a flow regulation system for the treatment of congestive heart failure. The flow regulation system regulates flow to use the bodies neural and physiological feedback systems to control the heart to relieve the heart of congestion. The present system also provides the ability to controllably allow the heart to recuperate and increase the heart rate to a normal level and thus allow for increased, normal cardiac output. This allows the heart to recuperate, and increases the efficiency of pharmacologically supplemented recuperation methods.

Although the present invention has been described with reference to preferred embodiments, workers skilled in the art will recognize that changes may be made in form and detail without departing from the spirit and scope of the invention.

What is claimed is:

1. A method of treating heart disease in a mammal having a coronary system including a heart, an ascending aorta, and a descending aorta, a renal system including renal arteries, and a physiological feedback system including baroreceptors and a renal response system controlling the heart, the method comprising:

providing a first regulator disposed in the descending aorta proximate the renal arteries and a second regulator disposed in the ascending aorta; and regulating flow of blood to the renal arteries from the descending aorta with the first regulator and regulating flow of blood in the ascending aorta to affect the physiological feedback system such that heart congestion is reduced.

2. The method of claim 1 wherein providing the first regulator comprises:

providing a first expandable member;

providing a second expandable member;

disposing the first expandable member in the descending aorta upstream of the renal arteries; and disposing the second expandable member in the descending aorta downstream of the renal arteries, wherein the first and second expandable members are expandable to have a dimension sufficient to substantially occlude the descending aorta.

3. The method of claim 2 and further comprising:

controlling expansion of the first and second expandable members to periodically increase blood flow to the renal arteries in excess of naturally occurring blood flow.

4. The method of claim 3 wherein expanding the first and second expandable members comprises:

contracting the first expandable member;

expanding the second expandable member to allow blood to pool in the descending aorta proximate the renal arteries; and then expanding the first expandable member to increase blood pressure and blood flow into the renal arteries.

5. The method of claim 4 and further comprising:

contracting the second expandable member after the first expandable member has been expanded.

6. The method of claim 4 and further comprising:

contracting the second expandable member as the first expandable member is being expanded.

7. The method of claim 4 wherein expanding the first expandable member and expanding the second expandable member comprises:

controlling expansion of the first and second expandable members based on a sinus rhythm of the heart.

8. The method of claim 2 wherein providing the second regulator comprises:

providing a third expandable member;

providing a fourth expandable member;

disposing the third expandable member in the aorta upstream of a baroreceptor proximate a heart; and disposing the fourth expandable member in the aorta downstream of the baroreceptor proximate the heart, wherein the third and fourth expandable members are expandable to have a dimension sufficient to substantially occlude the aorta.

9. The method of claim 8 and further comprising:

controlling expansion of the third and fourth expandable members to periodically decrease blood flow to the renal arteries in excess of naturally occurring blood flow.

10. The method of claim 1 wherein regulating flow of blood with the first regulator comprises:

increasing blood flow velocity to the renal arteries with the first regulator.

11. The method of claim 1 wherein regulating flow with the second regulator comprises:

decreasing blood flow velocity to the renal system with the second regulator.

12. The method of claim 1 wherein providing the second regulator comprises:

providing a first expandable member;

providing a second expandable member;

disposing the first expandable member in the aorta upstream of a baroreceptor proximate a heart; and disposing the second expandable member in the aorta downstream of the baroreceptor proximate the heart, wherein the first and second expandable members are expandable to have a dimension sufficient to substantially occlude the aorta.

13. The method of claim 12 and further comprising:

controlling expansion of the first and second expandable members to periodically decrease blood flow to the renal arteries in excess of naturally occurring blood flow.

14. The method of claim 1 wherein providing the first regulator comprises:

providing a pumping mechanism;

disposing the pumping mechanism in the descending aorta upstream of the renal arteries; and operating the pumping mechanism to selectively increase blood flow in the renal system above naturally occurring blood flow.

15. The method of claim 14 wherein providing the second regulator comprises:

providing a second pumping mechanism;

disposing the second pumping mechanism in the ascending aorta proximate a baroreceptor proximate the heart; and operating the pumping mechanism to selectively decrease blood pressure at the baroreceptor below naturally occurring blood pressure.

16. The method of claim 15 wherein the first and second pumping mechanisms each comprise expandable members.

17. The method of claim 16 wherein the first and second pumping mechanisms each comprise pumps having a passageway through which blood can flow.

* * * * *